United States Patent
Iwakiri et al.

(10) Patent No.: US 11,191,499 B2
(45) Date of Patent: Dec. 7, 2021

(54) RADIOGRAPHIC IMAGING APPARATUS

(71) Applicant: FUJIFILM Corporation, Tokyo (JP)

(72) Inventors: Naoto Iwakiri, Kanagawa (JP);
Keiichiro Sato, Kanagawa (JP);
Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 194 days.

(21) Appl. No.: 16/354,744

(22) Filed: Mar. 15, 2019

(65) Prior Publication Data
US 2019/0298281 A1 Oct. 3, 2019

(30) Foreign Application Priority Data

Apr. 2, 2018 (JP) .............................. JP2018-071223

(51) Int. Cl.
*A61B 6/00* (2006.01)
*H01L 27/146* (2006.01)
*G06T 7/00* (2017.01)

(52) U.S. Cl.
CPC .............. *A61B 6/42* (2013.01); *A61B 6/4208* (2013.01); *A61B 6/4283* (2013.01);
(Continued)

(58) Field of Classification Search
CPC ....... A61B 6/42; A61B 6/4208; A61B 6/4283; A61B 6/4291; A61B 2560/04; A61B 2562/02; A61B 2562/04; A61B 2562/046; A61B 2562/16; A61B 2562/164; G01N 2223/00; G01N 2223/50; G01N 2223/501;
(Continued)

(56) References Cited

U.S. PATENT DOCUMENTS 5,801,685 A * 9/1998 Miller .................. G11B 27/034
715/202
8,669,529 B2 3/2014 Watanabe et al.
(Continued)

FOREIGN PATENT DOCUMENTS

| JP | 2010-85121 A | 4/2010 |
|----|-------------|--------|
| JP | 2012-112725 A | 6/2012 |
| JP | 2014-240769 A | 12/2014 |

OTHER PUBLICATIONS

Japanese Office Action, dated Jul. 27, 2021, for corresponding Japanese Application No. 2018-071223, with an English machine translation.

*Primary Examiner* — Anastasia Midkiff
(74) *Attorney, Agent, or Firm* — Birch, Stewart, Kolasch & Birch, LLP

(57) ABSTRACT

A radiographic imaging apparatus includes a sensor substrate including a flexible base material, and an active area which is provided on a first surface of the base material and in which a plurality of pixels, which accumulate electrical charges generated in accordance with light converted from radiation, are formed; a conversion layer that is provided on the first surface side in the sensor substrate to convert radiation into the light; and a grid that is disposed on a second surface side opposite to the first surface of the base material and has a removal portion that has a mesh-like radiation absorbing member provided between a plurality of partitions in units of a predetermined number of pixels to remove scattered radiation according to the radiation.

10 Claims, 7 Drawing Sheets

(52) U.S. Cl.
CPC .. *H01L 27/14618* (2013.01); *H01L 27/14625* (2013.01); *H01L 27/14634* (2013.01); *A61B 6/548* (2013.01); *A61B 2562/16* (2013.01); *A61B 2562/164* (2013.01); *G01N 2223/501* (2013.01); *G06T 7/0012* (2013.01)

(58) Field of Classification Search
CPC ... H01L 27/14; H01L 27/144; H01L 27/1446; H01L 27/146; H01L 27/14601; H01L 27/14618; H01L 27/1462; H01L 27/14625; H01L 27/1463; H01L 27/14634; H01L 27/14665; H01L 27/14676; H01L 27/148; H01L 27/14806; H01L 27/14831; H01L 27/14893
See application file for complete search history.

(56) References Cited

U.S. PATENT DOCUMENTS

| | | | |
|---|---|---|---|
| 2004/0251420 A1* | 12/2004 | Sun | G01T 1/202 250/370.09 |
| 2012/0126128 A1 | 5/2012 | Watanabe et al. | |
| 2014/0361180 A1* | 12/2014 | Fujimura | H01L 27/14612 250/366 |
| 2017/0293039 A1* | 10/2017 | Blenk | A61B 6/102 |

\* cited by examiner

RADIOGRAPHIC IMAGING APPARATUS

CROSS-REFERENCE TO RELATED APPLICATION

The present application claims priority under 35 U.S.C § 119 to Japanese Patent Application No. 2018-071223, filed on Apr. 2, 2018, which is hereby expressly incorporated by reference, in its entirety, into the present application.

BACKGROUND

Technical Field

The present invention relates to a radiographic imaging apparatus.

Related Art

In the related art, radiographic imaging apparatuses that perform radiographic imaging for medical diagnosis have been known. A radiation detector for detecting radiation transmitted through a subject and generating a radiographic image is used for such radiographic imaging apparatuses.

As the radiation detector, there is one comprising a conversion layer, such as a scintillator, which converts radiation into light, and a sensor substrate in which a plurality of pixels, which accumulate electrical charges generated in accordance with light converted in the conversion layer, are provided. As such a radiation detector, it is known that a flexible base material is used for the sensor substrate. By using the flexible base material, for example, there is a case where the weight of the radiographic imaging apparatus (radiation detector) can be reduced and imaging of a subject becomes easy.

Meanwhile, in a case where the radiographic image is captured, in order to remove scattered radiation, which is generated by the radiation being transmitted through the subject, from the radiation transmitted through the subject, a technique of providing a grid on a side of the radiation detector where the radiation is radiated is known.

For example, JP2012-112725A discloses a radiographic imaging apparatus comprising a radiation detector comprising a sensor substrate using a flexible base material, and a grid in which a plurality of linear radiation absorbing members are provided.

In a case where the flexible base material is used for the sensor substrate, the thickness of the base material is smaller than that of a non-flexible base material in many cases. Since the thickness is small, the radiation dose of the scattered radiation absorbed by the base material itself is smaller in the flexible base material than in the non-flexible base material.

For that reason, in a case where the flexible base material is used, in the grid in which the plurality of linear radiation absorbing members are provided, there is a case where the scattered radiation cannot be sufficiently absorbed and there is a case where the image quality of the radiographic image deteriorates under the influence of the scattered radiation.

SUMMARY

The present disclosure is to provide a radiographic imaging apparatus that can improve the image quality of a radiographic image compared to a configuration including a grid in which a plurality of linear radiation absorbing members are provided.

In order to achieve the above object, a radiographic imaging apparatus of a first aspect of the present disclosure comprises a sensor substrate including a flexible base material, and a pixel region which is provided on a first surface of the base material and in which a plurality of pixels, which accumulate electrical charges generated in accordance with light converted from radiation, are formed; a conversion layer that is provided on the first surface side in the sensor substrate to convert radiation into the light; and a grid that is disposed on a second surface side opposite to the first surface of the base material and has a removal portion that has a mesh-like radiation absorbing member provided between a plurality of partitions in units of a predetermined number of pixels to remove scattered radiation according to the radiation.

Additionally, in the radiographic imaging apparatus of a second aspect of the present disclosure based on the first aspect, the removal portion is disposed in a region corresponding to the pixel region of the sensor substrate, and the grid further has an absorption portion provided with a planar radiation absorbing member that covers a region, corresponding to an outside of the pixel region within a predetermined range from the pixel region, on the second surface the base material.

Additionally, in the radiographic imaging apparatus of a third aspect of the present disclosure based on the first aspect, the base material has a polygonal shape in a plan view as seen from the first surface side, and a region, corresponding to the outside of the pixel region, at one side of the polygonal shape is bent toward the conversion layer side.

Additionally, in the radiographic imaging apparatus of a fourth aspect of the present disclosure based on the third aspect, the polygonal shape is a rectangular shape.

Additionally, the radiographic imaging apparatus of a fifth aspect of the present disclosure based on the third or fourth aspect further comprises a housing that houses the sensor substrate, the conversion layer, and the grid, and a distance between the sensor substrate and an inner surface of the housing that faces the sensor substrate is shorter on a side where the base material of the sensor substrate is bent than on a side opposite to the bent side.

Additionally, the radiographic imaging apparatus of a sixth aspect of the present disclosure based on any one of the first to fourth aspect further comprises a housing that comprises an imaging surface irradiated with radiation and houses the sensor substrate, the conversion layer, and the grid in a state where the sensor substrate is disposed closer to the imaging surface side than the conversion layer.

Additionally, in the radiographic imaging apparatus of a seventh aspect of the present disclosure based on any one of the first to sixth aspect, a width of the meshes is the same as an interval between the plurality of partitions.

Additionally, the radiographic imaging apparatus of an eighth aspect of the present disclosure based on any one of the first to seventh aspect further comprises a protective film that covers an entire laminated body in which the sensor substrate, the conversion layer, and the grid are laminated.

Additionally, the radiographic imaging apparatus of a ninth aspect of the present disclosure based on any one of the first to seventh aspect further comprises a protective film that covers an entire laminated body in which the sensor substrate and the conversion layer are laminated.

Additionally, in the radiographic imaging apparatus of a tenth aspect of the present disclosure based on any one of the first to ninth aspect, the base material has a first alignment mark for alignment, and the grid has a second alignment mark corresponding to the first alignment mark.

Additionally, in the radiographic imaging apparatus of an eleventh aspect of the present disclosure based on any one of the first to tenth aspect further comprises an elastic layer provided on a side of the conversion layer opposite to a side where the sensor substrate is provided.

According to the first aspect of the present disclosure, the image quality of the radiographic image can be improved compared to a configuration including a grid in which a plurality of linear radiation absorbing members are provided.

According to the second aspect of the present disclosure, the image quality of the radiographic image can be further improved compared to a case where the grid does not have the removal portion and the absorption portion.

According to the third aspect of the present disclosure, the radiographic imaging apparatus can be applied to a mammography apparatus compared to a case where the region, corresponding to the outside of the pixel region, at one side of the polygonal shape of the base material is not bent toward the conversion layer side.

According to the fourth aspect of the present disclosure, the radiographic imaging apparatus is more preferably applied to the mammography apparatus compared to a case where the shape of the base material is not the rectangular shape.

According to the fifth aspect of the present disclosure, the radiographic imaging apparatus can be applied to the mammography apparatus compared to a case where the distance between the sensor substrate and the inner surface of the housing that faces the sensor substrate is longer on the side where the base material of the sensor substrate is bent than on the side opposite to the bent side.

According to the sixth aspect of the present disclosure, the scattered radiation that reaches the sensor substrate can be appropriately suppressed compared to a case where the sensor substrate is housed within the housing in a state where the sensor substrate is not disposed closer to the imaging surface side than the conversion layer.

According to the seventh aspect of the present disclosure, more scattered radiation can be absorbed compared to a case where the width of the meshes is not the same as an interval between the plurality of partitions.

According to the eighth aspect of the present disclosure, a moisture resistance effect can be further enhanced compared to a configuration in which the protective film does not cover the entire laminated body in which the sensor substrate, the conversion layer, and the grid are laminated.

According to the ninth aspect of the present disclosure, a moisture resistance effect can be further enhanced compared to a configuration in which the protective film does not cover the entire laminated body in which the sensor substrate and the conversion layer are laminated.

According to the tenth aspect of the present disclosure, the grid can be easily disposed on the base material compared to a case where the base material and the grid does not have the first alignment mark and the second alignment mark, respectively.

According to the eleventh aspect of the present disclosure, the sensor substrate can be easily returned to a state before deflection in a case where deflection occurs in the sensor substrate compared to a case where the elastic layer is not comprised.

DESCRIPTION OF EMBODIMENTS

Hereinafter, embodiments of the invention will be described in detail with reference to the drawings. In addition, the present embodiments do not limit the invention.

A radiographic imaging apparatus of the present embodiment has a function of capturing a radiographic image of an object to be imaged, by detecting radiation transmitted through a subject, which is the object to be imaged, and outputting image information representing a radiographic image of the subject.

Figure 1:
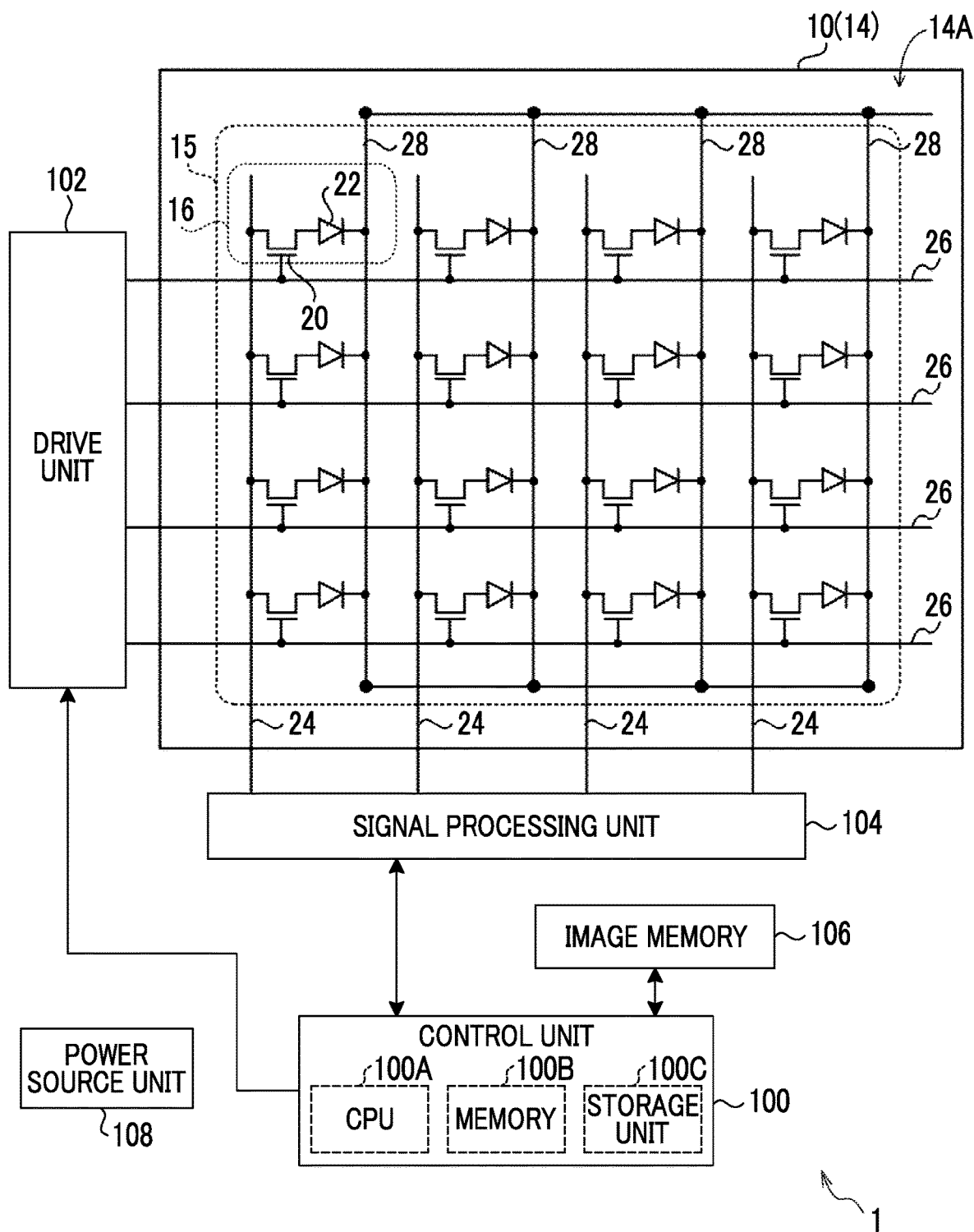
FIG. 1 is a block diagram illustrating an example of the configuration of main parts of an electrical system in a radiographic imaging apparatus of a first embodiment.

First, the outline of an example of the configuration of an electrical system in the radiographic imaging apparatus of the present embodiment will be described with reference to FIG. 1. FIG. 1 is a block diagram illustrating an example of the configuration of main parts of the electrical system in the radiographic imaging apparatus of the present embodiment.

As illustrated in FIG. 1, the radiographic imaging apparatus 1 of the present embodiment comprises a radiation detector 10, a control unit 100, a drive unit 102, a signal processing unit 104, an image memory 106, and a power source unit 108.

The radiation detector 10 comprises a sensor substrate 12 (refer to FIG. 2) and a conversion layer 30 (refer to FIG. 2) that converts radiation into light. The sensor substrate 12 comprises a flexible base material 14 and a plurality of pixels 16 provided on a first surface 14A of the base material 14. In addition, in the following, the plurality of pixels 16 may be simply referred to as "pixels 16".

As illustrated in FIG. 1, each pixel 16 of the present embodiment comprises a sensor part 22, such as a photodiode, which generates and accumulates an electrical charge in accordance with the light converted by the conversion layer, and a switching element 20 that reads the electrical charge accumulated in the sensor part 22. In the present embodiment, as an example, a thin film transistor (TFT) is used as the switching element 20. For that reason, in the following, the switching element 20 is referred to as a "TFT 20". In the present embodiment, a layer in which the pixels 16 are formed on the first surface 14A of the base material 14 is provided as a flattened layer in which the sensor parts 22 and the TFTs 20 are formed. In the following, there is a case where the layer in which the pixels 16 are formed is also referred to as the "pixels 16" for convenience of description.

The pixels 16 are two-dimensionally disposed in one direction (a scanning wiring direction corresponding to a transverse direction of FIG. 1, hereinafter referred to as a "row direction"), and a direction intersecting the row direction (a signal wiring direction corresponding to the longitudinal direction of FIG. 1, hereinafter referred as a "column direction") in an active area 15 of the sensor substrate 12. Although an array of the pixels 16 are illustrated in a simplified manner in FIG. 1, for example, 1024×1024 pixels 16 are disposed in the row direction and the column direction.

Additionally, a plurality of scanning wiring lines 26, which are provided for respective rows of the pixels 16 to control switching states (ON and OFF) of the TFTs 20, and a plurality of signal wiring lines 24, which are provided for respective columns of the pixels 16 and from which electrical charges accumulated in the sensor parts 22 are read, are provided in a mutually intersecting manner in the radiation detector 10. The plurality of scanning wiring lines 26 are electrically connected to a drive unit 102, respectively. The control unit 100 to be described below is connected to the drive unit 102 which outputs driving signals in accordance with a control signal output from the control unit 100. Driving signals, which are output from the drive unit 102 to drive the TFTs 20 to control the switching states thereof, flow to the plurality of scanning wiring lines 26, respectively. Additionally, the plurality of signal wiring lines 24 are electrically connected to the signal processing unit 104, respectively, and thereby, electrical charges read from the respective pixels 16 are output to the signal processing unit 104 as electrical signals. The signal processing unit 104 generates and outputs image data according to the input electrical signals.

The control unit 100 to be described below is connected to the signal processing unit 104, and the image data output from the signal processing unit 104 is sequentially output to the control unit 100. The image memory 106 is connected to the control unit 100, and the image data sequentially output from the signal processing unit 104 is sequentially stored in the image memory 106 under the control of the control unit 100. The image memory 106 has a storage capacity capable of storing image data equivalent to a predetermined number of sheets, and whenever radiographic images are captured, image data obtained by the capturing is sequentially stored in the image memory 106.

The control unit 100 comprises a central processing unit (CPU) 100A, a memory 100B including a read only memory (ROM), a random access memory (RAM), and the like, and a nonvolatile storage unit 100C, such as a flash memory. An example of the control unit 100 is a microcomputer or the like. The control unit 100 controls the overall operation of the radiographic imaging apparatus 1.

Additionally, common wiring lines 28 are provided in a wiring direction of the signal wiring lines 24 at the sensor parts 22 of the respective pixels 16 in order to apply bias voltages to the respective pixels 16. Bias voltages are applied to the respective pixels 16 from a bias power source by electrically connecting the common wiring lines 28 to the bias power source (not illustrated) outside the sensor substrate 12.

The power source unit 108 supplies electrical power to various elements or various circuits, such as the control unit 100, the drive unit 102, the signal processing unit 104, the image memory 106, and the power source unit 108. In addition, in FIG. 1, illustration of wiring lines, which connect the power source unit 108 and various elements or various circuits together, is omitted in order to avoid complication.

Figure 2:
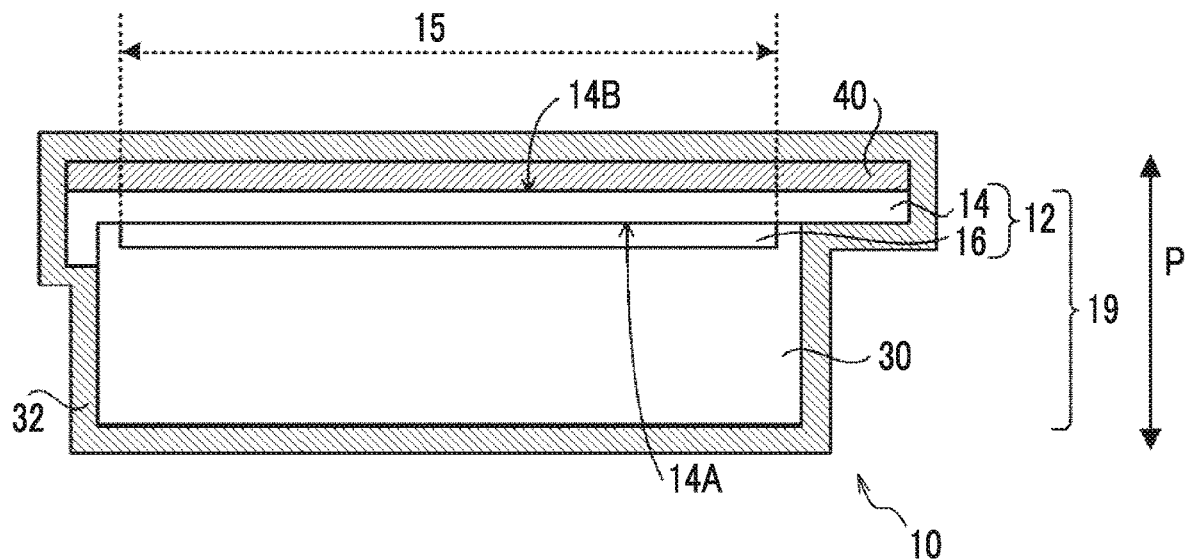
FIG. 2 is a cross-sectional view of an example of a radiation detector of the embodiment.

Moreover, the radiation detector 10 of the present embodiment will be described in detail. FIG. 2 is a cross-sectional view of an example of the radiation detector 10 of the present embodiment.

As illustrated in FIG. 2, the radiation detector 10 of the present embodiment comprises the sensor substrate 12 including the base material 14 and the pixels 16, the conversion layer 30, a protective film 32. Additionally, in the radiation detector 10 of the present embodiment, a laminated body 19 in which the sensor substrate 12 and the conversion layer 30 are laminated and a grid 40 are integrally configured.

In addition, in the following, a direction (upward-downward direction in FIG. 2) in which the grid 40, the base material 14, the pixels 16, and the conversion layer 30 are arranged is referred to as a lamination direction (refer to a lamination direction P in FIG. 2). Additionally, for convenience of description, the conversion layer 30 side of the radiation detector 10 in the lamination direction P may be referred to as "up", and the sensor substrate 12 side may be referred to as "down." Additionally, "thickness" refers to a thickness in the lamination direction P.

The base material 14 is a resin sheet having flexibility and including, for example, plastics, such as polyimide. A specific example of the base material 14 is XENOMAX (registered trademark). In addition, the base material 14 may have any desired flexibility and is not limited to the resin sheet. For example, the base material 14 may be a relatively thin glass substrate. The thickness of the base material 14 may be a thickness such that desired flexibility is obtained in accordance with the hardness of a material, the size of the sensor substrate 12 (the area of the first surface 14A or the second surface 14B), or the like. As an example having flexibility, in the case of a single rectangular base material 14, in a state where one side of the base material 14 is fixed, the base material 14 hangs down 2 mm or more with the gravity resulting from its own weight at a position 10 cm away from the fixed side (become lower than the height of the fixed side). As a specific example in a case where the base material 14 is the resin sheet, the thickness thereof may be 5 µm to 125 µm. As a specific example in a case where the base material 14 is the glass substrate, the base material 14 has flexibility in a case where the thickness thereof becomes 0.1 mm or less in a size in which one side is about 43 cm or less. Therefore, the thickness may be 0.1 mm or less.

The base material 14 of the present embodiment has a rectangular shape having a pair of long sides and a pair of short sides in a plan view as seen from the first surface 14A. Additionally, the sensor substrate 12 also has a rectangular shape similarly to the shape of the base material 14.

As illustrated in FIG. 2, the plurality of pixels 16 are provided in an inner partial region on the first surface 14A of the base material 14. In other words, in the sensor substrate 12 of the present embodiment, no pixel 16 is provided at an outer peripheral part of the first surface 14A of the base material 14. In the present embodiment, the region on the first surface 14A of the base material 14 where the pixels 16 are provided is used as the active area 15. The active area 15 of the present embodiment is an example of the pixel region of the present disclosure. In addition, in the present embodiment, as an example, the pixels 16 are provided on the first surface 14A of the base material 14 via an undercoat layer (not illustrated) using SiN or the like.

Additionally, as illustrated in FIG. 2, the conversion layer 30 covers the active area 15. The conversion layer 30 of the present embodiment covers a range wider than the active area 15, including the entire active area 15, as an example.

In the present embodiment, a scintillator including CsI (cesium iodide) is used as an example of the conversion layer 30. It is preferable that such a scintillator includes, for example, CsI:Tl (cesium iodide to which thallium is added) or CsI:Na (cesium iodide to which sodium is added) having an emission spectrum of 400 nm to 700 nm at the time of X-ray radiation. In addition, the emission peak wavelength in a visible light region of CsI:Tl is 565 nm.

In the radiation detector 10 of the present embodiment, as an example, the conversion layer 30 of CsI is directly formed as a columnar crystal on the sensor substrate 12 by a vapor deposition method, such as a vacuum vapor deposition method, a sputtering method, and a chemical vapor deposition (CVD) method. As a method of forming the conversion layer 30 includes, for example, in a case where CsI:Tl is used as the conversion layer 30, there is a vacuum vapor deposition method in which CsI:Tl with heating means, such as a resistance heating-type crucible, is heated and gasified in an environment with the vacuum degree of 0.01 Pa to 10 Pa, and CsI:Tl is deposited on the sensor substrate 12 with the temperature of the sensor substrate 12 as the room temperature (20°) to 300° C. As the thickness of the conversion layer 30, 100 μm to 800 μm is preferable.

In addition, in the present embodiment, an end part of a columnar crystal of the conversion layer 30 on a base point side (a sensor substrate 12 side in the present embodiment) in a growth direction is referred to as a "root", and a sharpened end part opposite to the root in the growth direction is referred to as a "tip".

In addition, in this way, in a case where the conversion layer of CsI is directly formed on the sensor substrate 12 by the vapor deposition method, for example, a reflective layer (not illustrated) having a function of reflecting the light converted in the conversion layer 30 may be provided on the surface of the conversion layer opposite to the side in contact with the sensor substrate 12. The reflective layer may be directly provided in the conversion layer 30, and or may be provided via an adhesion layer or the like. As a material of the reflective layer in this case, it is preferable to use an organic material, and it is preferable to use, for example, at least one of white polyethylene terephthalate (PET), $TiO_2$, $Al_2O_3$, foamed white PET, a polyester-based high-reflection sheet, specular reflection aluminum, or the like. Particularly, it is preferable to use the white PET as the material from a viewpoint of reflectivity.

In addition, the white PET is obtained by adding a white pigment, such as $TiO_2$ or barium sulfate, to PET. Additionally, the polyester-based high-reflection sheet is a sheet (film) having a multilayer structure in which a plurality of thin polyester sheets are laminated. Additionally, the foamed white PET is white PET of which the surface is porous.

Additionally, in a case where the scintillator of CsI is used as the conversion layer 30, the conversion layer 30 can also be formed in the sensor substrate 12 by a method different from the method of the present embodiment. For example, the conversion layer 30 may be formed in the sensor substrate 12 by preparing CsI vapor-deposited on an aluminum sheet or the like by the vapor deposition method, and bonding the side of CsI, which is not in contact with the aluminum sheet, and the pixels 16 of the sensor substrate 12 together with an adhesive sheet or the like.

Moreover, unlike the radiation detector 10 of the present embodiment, GOS ($Gd_2O_2S$:Tb) or the like may be used as the conversion layer 30 instead of CsI. In this case, for example, a sheet bonded to a support formed of the white PET or the like with an adhesion layer or the like is prepared as a sheet in which GOS is dispersed in a binder, such as resin. The conversion layer 30 can be formed in the sensor substrate 12 by bonding the side of GOS on which the support is not bonded, and the pixels 16 of the sensor substrate 12 together with an adhesive sheet or the like. In addition, the efficiency of conversion from radiation to visible light in a case where CsI is used for the conversion layer 30 becomes higher than that in a case where GOS is used.

In the radiation detector 10 of the present embodiment, as illustrated in FIG. 2, a region, corresponding to the outside of the active area 15, at one side of the pair of short sides of the base material 14 having the rectangular shape is bent toward the conversion layer 30 side. Accordingly, an end part of the conversion layer 30 is covered with the base material 14 in the above one side.

Figure 3:
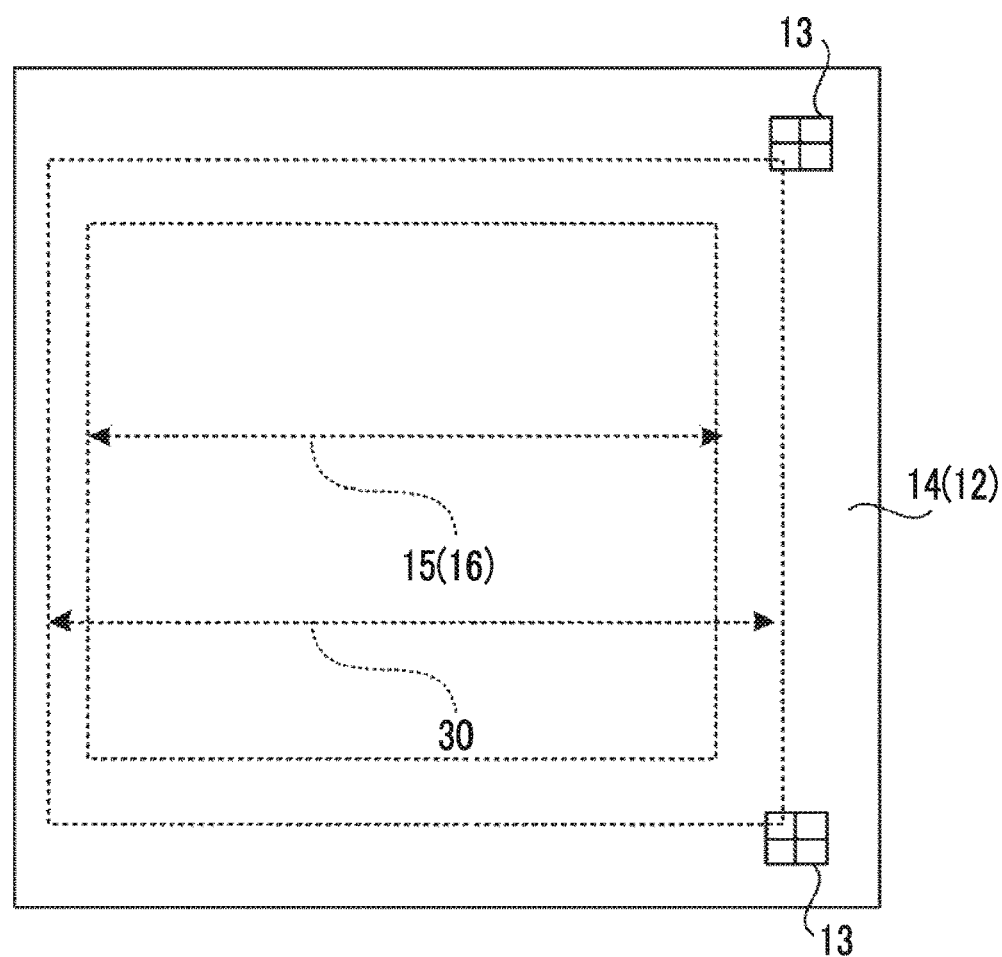
FIG. 3 is a plan view of an example of a laminated body, in which a sensor substrate and a conversion layer of the embodiment are laminated, as seen from a sensor substrate side.

A plan view of the laminated body 19 in which the sensor substrate 12 and the conversion layer 30 are laminated, as seen from the sensor substrate 12 side (the second surface 14B side of the base material 14), is illustrated in FIG. 3. On the second surface 14B of the base material 14, an alignment mark 13 used for the alignment in the case of disposing a grid 40 is provided in a region corresponding to the outside of the active area 15. In the present embodiment, as an example, two alignment marks 13 are provided in the vicinity of both end parts of a side of the base material 14 opposite to a bent side of the base material 14. However, positions where the alignment marks 13 are provided may be regions corresponding to the outside of the active area 15. In addition, the numbers and the positions of the alignment marks 13 to be provided, and the sizes, the shapes, and the like of the alignment marks 13 are not particularly limited. The alignment marks 13 of the present embodiment are an example of a first alignment mark of the present disclosure.

Figure 4:
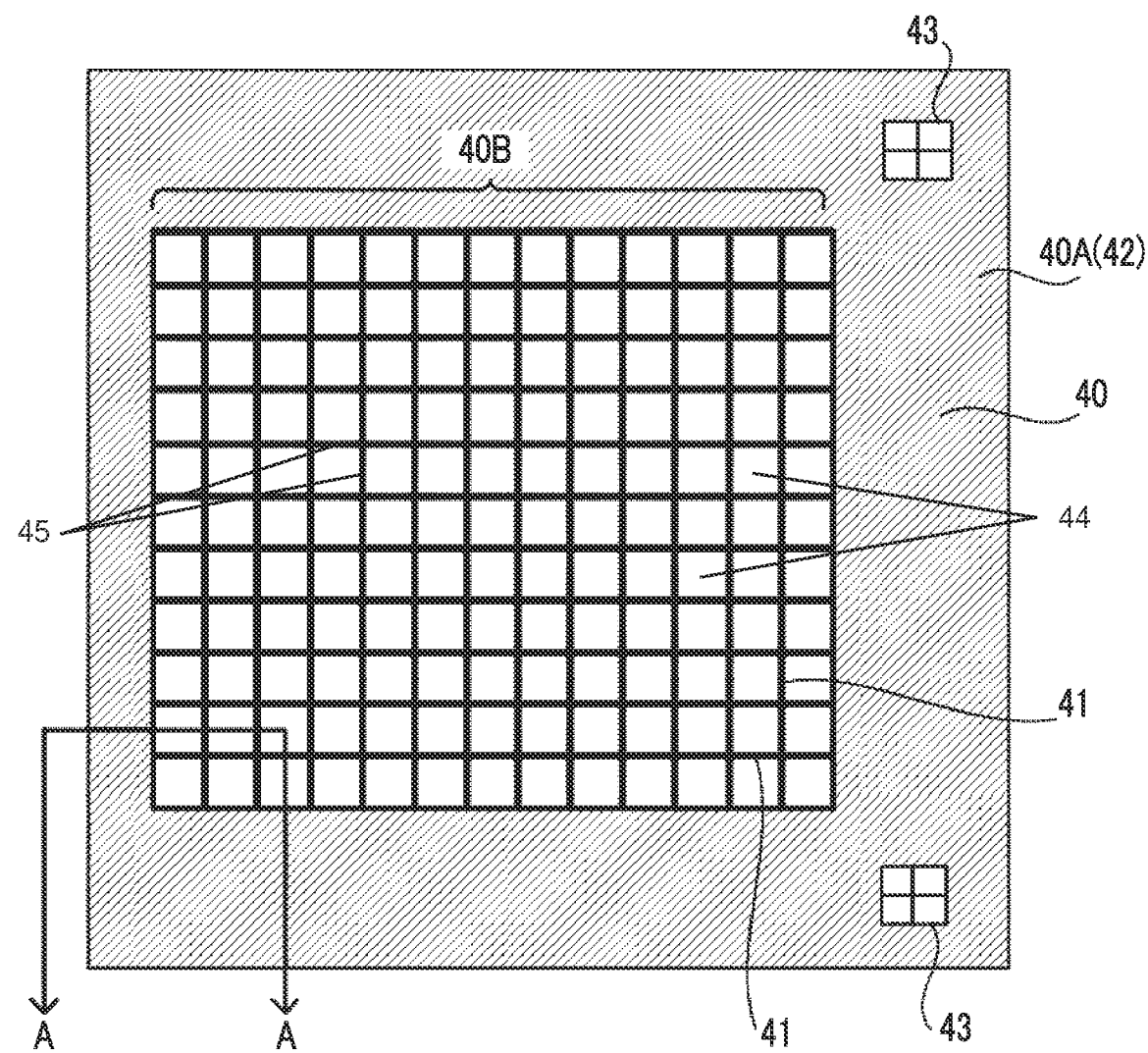
FIG. 4 is a plan view an example of a grid of the embodiment as seen from a side opposite to a side where the sensor substrate is provided.
Figure 5:
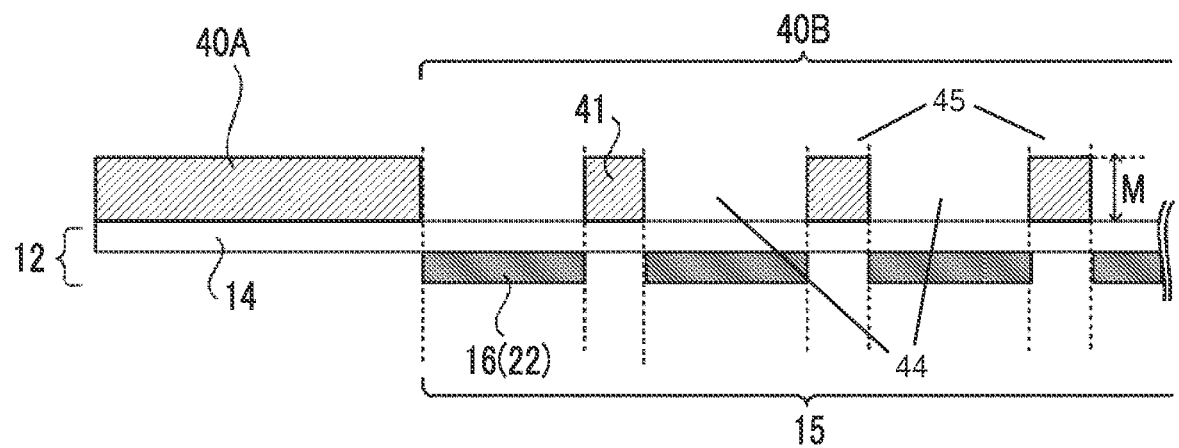
FIG. 5 is a cross-sectional view, taken along line A-A, of the grid illustrated in FIG. 4.

Additionally, as illustrated in FIG. 2, the grid 40 of the present embodiment is disposed on the second surface 14B side of the base material 14. A plan view the grid 40 of the present embodiment as seen from a side opposite to a side where the sensor substrate 12 is provided is illustrated in FIG. 4. Additionally, FIG. 5 is a cross-sectional view of the grid 40 taken along line A-A in FIG. 4. In addition, for convention of description, the pixels 16 (sensor parts 22) are also illustrated in FIG. 5.

As illustrated in FIG. 4, the grid 40 of the present embodiment has an absorption portion 40A and a removal portion 40B. The removal portion 40B is provided with a mesh-like radiation absorbing member 41. As illustrated in FIG. 5, the radiation absorbing member 41 is provided on the second surface 14B side of the base material 14 in a state where meshes 45 correspond to between a plurality of partitions 44 partitioned for a predetermined number of pixels. In the present embodiment, as an example, the above predetermined number is set to "1", and the meshes of the radiation absorbing member 41 correspond to between a plurality of partitions 44 partitioned for every pixel, in other words, between respective pixels. That is, in the radiation detector 10 of the present embodiment, the active area 15 is divided into partitions 44 for every pixel by the meshes of the radiation absorbing member 41. Additionally, in the present embodiment, the width of the meshes 45 of the radiation absorbing member 41 is made equal to an interval between a pixel 16 and a pixel 16.

Figure 6:
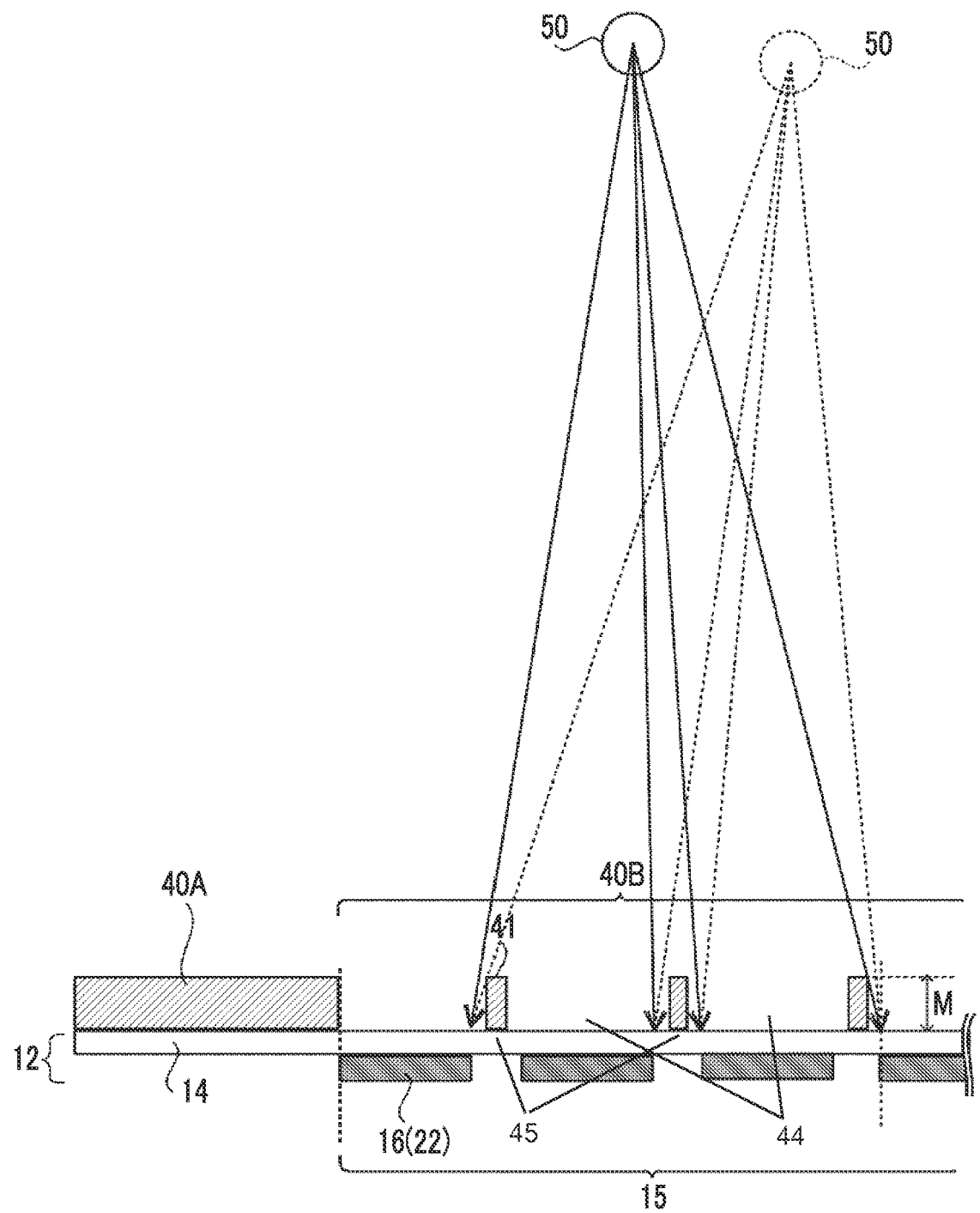
FIG. 6 is an explanatory view for explaining the width of a mesh in the grid of the present embodiment.
Figure 7:
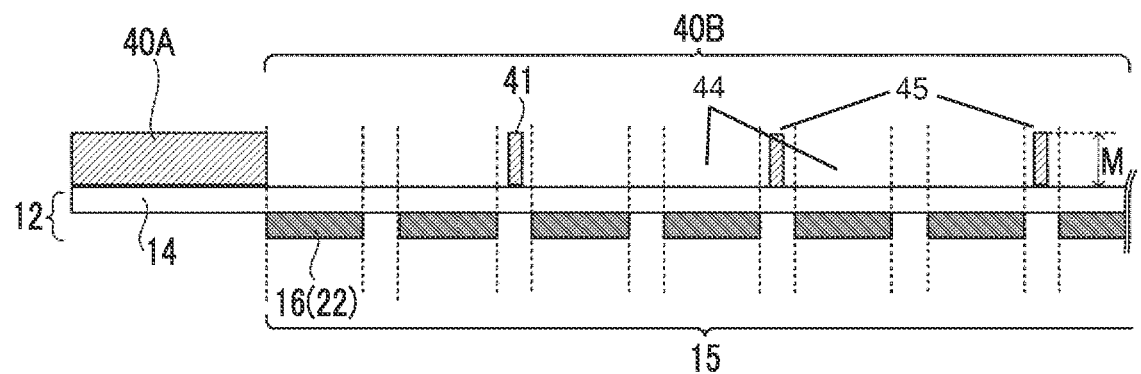
FIG. 7 is a cross-sectional view of another example of the grid of the present embodiment.

In addition, although the width of the meshes of the radiation absorbing member 41 is not limited to the present embodiment, it is preferable that the width is equal to or less than the interval between a pixel 16 and a pixel 16. A state where no meshes are provided in regions corresponding to the pixels 16 is preferable. Referring to FIG. 5, it is preferable that the meshes 45 of the radiation absorbing member 41 are not placed on the pixels 16 across the base material 14. In addition, in a case where tomography is performed, the angle of incidence of the radiation that is radiated to the radiation detector 10 varies by about ±20° because a plurality of radiographic images are captured while changing an angle at which a subject is irradiated with radiation from a radiation source including a tube. For that reason, in order to reduce occurrence of vignetting resulting from oblique incidence of the radiation, as illustrated in FIG. 6, it is desirable that the width of the meshes 45 is smaller in accordance with a distance between the sensor substrate 12 and the radiation source (tube) 50. Additionally, as illustrated in FIG. 7, for example, the above predetermined number may be set to "2".

Additionally, although the number (refer to the above "predetermined number of pixels") of pixels to be included in the partitions 44 divided by the meshes of the radiation absorbing member 41 is not limited, the intervals of the meshes 45 become closer as the number of pixels is smaller. Therefore, the quantity of scattered radiation absorbed can be increased, and the scattered radiation from a plurality of directions can be absorbed. Therefore, compared to a configuration in which only the scattered radiation from one direction is suppressed by a grid in which a plurality of linear radiation absorbing members are provided, in the mesh structure, the scattered radiation can be further suppressed and the image quality of the radiographic image can be improved.

Additionally, in the meshes 45 of the radiation absorbing member 41, the transmittance is preferably about 10% to 70%, for example, in a range of the tube voltage of the tube in the mammography, and the thickness M is preferably about 10 to 35 μm, for example, in a case where copper is used as a mesh material.

Additionally, as illustrated in FIG. 4, the absorption portion 40A is provided with the planar radiation absorbing member 42 that covers a region, corresponding to the outside of the active area within a predetermined range from the active area 15, on the second surface 14B of the base material 14. In the present embodiment, as an example, the absorption portion 40A covers the entire region, corresponding to the outside of the active area 15, on the second surface 14B of the base material 14. In addition, the region covered with the radiation absorbing member 42 of the absorption portion 40A is not limited to the present embodiment, and may be the region corresponding to the outside of the active area 15.

In the absorption portion 40A, alignment marks 43 to be used for alignment in a case where the absorption portion 40A is disposed on the sensor substrate 12 (base material 14) are provided at positions corresponding to the alignment marks 13 of the base material 14. In addition, the alignment marks 43 may have positions and shapes corresponding to the alignment marks 13, and the number and the positions of alignment marks 43 to be provided, and the sizes, the shapes, or the like thereof are not particularly limited similar to the case of the above-described alignment marks 13. The alignment marks 43 of the present embodiment are an example of a second alignment mark of the present disclosure.

The same material is used for the radiation absorbing member 41 and the radiation absorbing member 42. Although members, such as metals, such as gold, tantalum, lead, molybdenum, copper, silver, and aluminum, in which the capacity to absorb radiation is high are used and general grid materials can be used, it is preferable to use heavy metals because the thickness of the grid 40 can be thinned. Additionally, it is preferable that the radiation absorbing member 41 and the radiation absorbing member 42, are integrally formed.

The scattered radiation generated within the subject by radiating the radiation is radiation referred to as so-called soft X-rays in which the energy thereof is lower than that of the radiation irradiated to the subject, and tends to be easily transmitted through the base material 14 of the sensor substrate 12. In the radiation detector 10 (radiographic imaging apparatus 1) of the present embodiment, the grid 40 is provided as described above. Accordingly, the scattered radiation generated within the subject is absorbed by the radiation absorbing member 41 of the removal portion 40B to remove the scattered radiation included in the radiation that reaches the sensor substrate 12. Therefore, contrast degradation and defocusing resulting from the scattered radiation can be reduced.

Figure 8:
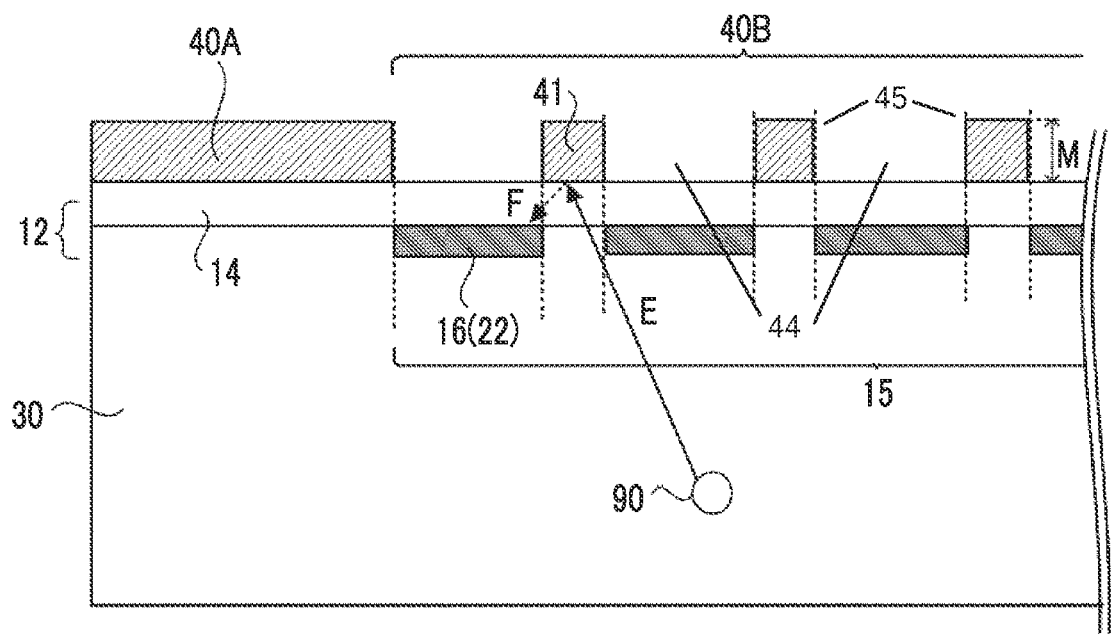
FIG. 8 is an explanatory view for explaining effects of the grid of the present embodiment.

Additionally, as illustrated in FIG. 8, light 90 (refer to solid arrow E in FIG. 8), which is generated in the conversion layer 30 in accordance with the radiated radiation, passes between the pixels 16, and is transmitted through the base material 14, is reflected at an interface of the base material 14 with the air in a case where the radiation absorbing member 41 is not provided unlike the radiation detector 10 of the present embodiment. Additionally, in this case, since the thickness of the flexible base material 14 is small, the light transmitted through the base material 14 is reflected in a direction of arrow F without a significant attenuation. In this case, since the light 90 is radiated from a back surface (a surface on the base material 14 side) of the sensor part 22 of each pixel 16, crosstalk is likely to occur. However, in the radiation detector 10 of the present embodiment, it is possible to prevent reflection in a direction indicated by arrow F of dotted line by forming the radiation absorbing member 41 of the removal portion 40B of the grid 40 in black or forming the radiation absorbing member 41 so as to have an absorption or reflection preventing effect with respect to the light emission wavelength of the conversion layer. That is, according to the radiation detector 10 of the present embodiment, as described above, the radiation absorbing member 41 suppresses the reflection of the light 90 at the interface of the base material 14 by being formed so as to have the absorption or reflection preventing effect. Therefore, the crosstalk can be reduced. Therefore, according to the radiation detector 10 of the present embodiment, a modulation transfer function (MTF) can be improved.

Additionally, in the radiation detector 10 of the present embodiment, as illustrated in FIG. 2, the protective film 32 covers the entire laminated body in a state where the laminated body 19 and the grid 40 are laminated. In other words, the protective film 32 covers the entire laminated body in which the grid 40, the sensor substrate 12, and the conversion layer 30 are laminated.

As the protective film 32, for example, a moisture resistance film, such as a PARYLENE (registered trademark) film, or an insulating sheet, such as polyethylene terephthalate, is used.

Figure 9:
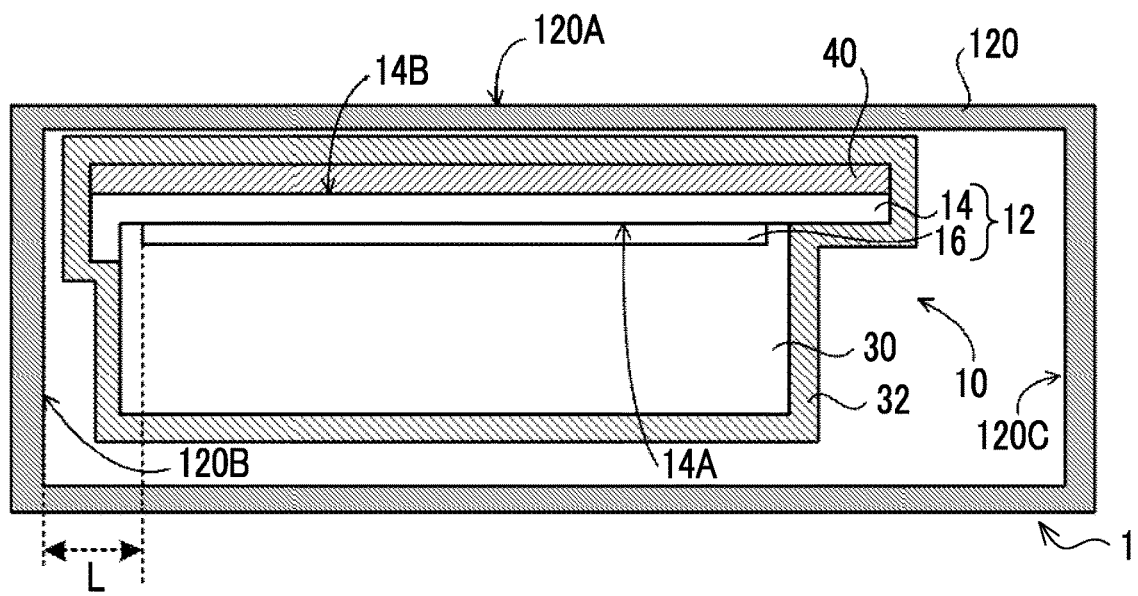
FIG. 9 is a cross-sectional view illustrating an example of a state where the radiation detector of the present embodiment is provided within a housing.

In a case where the above-described radiation detector 10 is used for the radiographic imaging apparatus 1, the radiation detector 10 is provided within a housing 120 as in an example illustrated in FIG. 9.

FIG. 9 is a cross-sectional view illustrating an example of a state where the radiation detector 10 is provided within a housing 120 in a case where the radiographic imaging apparatus 1 of the present embodiment is applied to an irradiation side sampling (ISS) type. In addition, the ISS type refers to a type that is used in a state where the sensor substrate 12 of the laminated body 19 is located on a radiation incidence side and the conversion layer 30 of the laminated body 19 is located on a radiation emission side. In the present embodiment, the radiation detector 10 is provided within the housing 120 in a state where the base material 14 of the radiation detector 10 faces the imaging surface 120A side of the housing 120.

As illustrated in FIG. 9, a distance between an inner surface 120B of the housing 120 and the radiation detector 10 (sensor substrate 12) is shorter than a distance between an inner surface 120C and the radiation detector 10 (sensor substrate 12). In a case where the radiographic imaging apparatus 1 is applied to a mammography apparatus, it is necessary to bring the active area 15 of the radiation detector 10 close to a chest wall side of the subject. For that reason, as illustrated in FIG. 9, a distance between the inner surface 120B on the chest wall side of the subject and the sensor substrate 12 is short. Additionally, in the radiation detector 10 of the present embodiment, the distance between the inner surface 120B and the sensor substrate 12 is shortened in a case where the base material 14 is bent toward the conversion layer 30 side as described above. In addition, a maximum value of a distance L between the inner surface 120B and the facing active area 15 is determined by the standard.

As described above, the radiographic imaging apparatus 1 of the above embodiment comprises the sensor substrate 12 including the flexible base material 14, and the active area 15 which is provided on the first surface 14A of the base material 14 and in which the plurality of pixels 16, which accumulate electrical charges generated in accordance with light converted from radiation, are formed; the conversion layer 30 that is provided on the first surface 14A side in the sensor substrate 12 to convert radiation into light; and the grid 40 that is disposed on the second surface 14B side opposite to the first surface 14A of the base material 14 and has the removal portion 42B that has the mesh-like radiation absorbing member 42 provided between the plurality of partitions 44 in units of the predetermined number of pixels to remove the scattered radiation according to the radiation.

In the radiographic imaging apparatus 1 of the present embodiment, compared with a configuration comprising a grid provided with a simple linear radiation absorbing member, the scattered radiation that reaches the sensor substrate 12 can be suppressed. Additionally, it is possible to suppress that the light 90 generated in the conversion layer 30 is reflected at the interface between the base material 14 and the air and enters from the back surface of each sensor part 22. Therefore, according to the radiographic imaging apparatus of the present embodiment, the scattered radiation of the radiation can be suppressed, the crosstalk of light occurring in the conversion layer can be suppressed, and the image quality of the radiographic image can be improved.

There is a problem that absorption is large in the non-flexible base material in applying the ISS type radiographic imaging apparatus to the mammography. For example, in non-alkali glass that has a thickness of 0.7 mm and is mainly used for normal TFTs, under the conditions that a Mo tube/Mo filter is used and the tube voltage is 24 kV, the X-rays transmittance of the base material 14 is about 20%, only about 20% of the X-rays have reached the conversion layer 30. Meanwhile, in a polyimide substrate (thickness is 0.04 mm) made of a flexible base material, even under the conditions that the Mo tube/Mo filter is used and the tube voltage is 24 kV, the X-rays transmittance of the base material 14 is 99.6%, and loss can be almost eliminated. Particularly, in the radiographic imaging apparatus 1 of the present embodiment, the scattered radiation can be sufficiently absorbed as described above even in a case where the flexible base material 14 is used. Therefore, even in a case where the ISS type radiographic imaging apparatus 1 is applied to the mammography apparatus, the image quality of the radiation can be improved.

Figure 10:
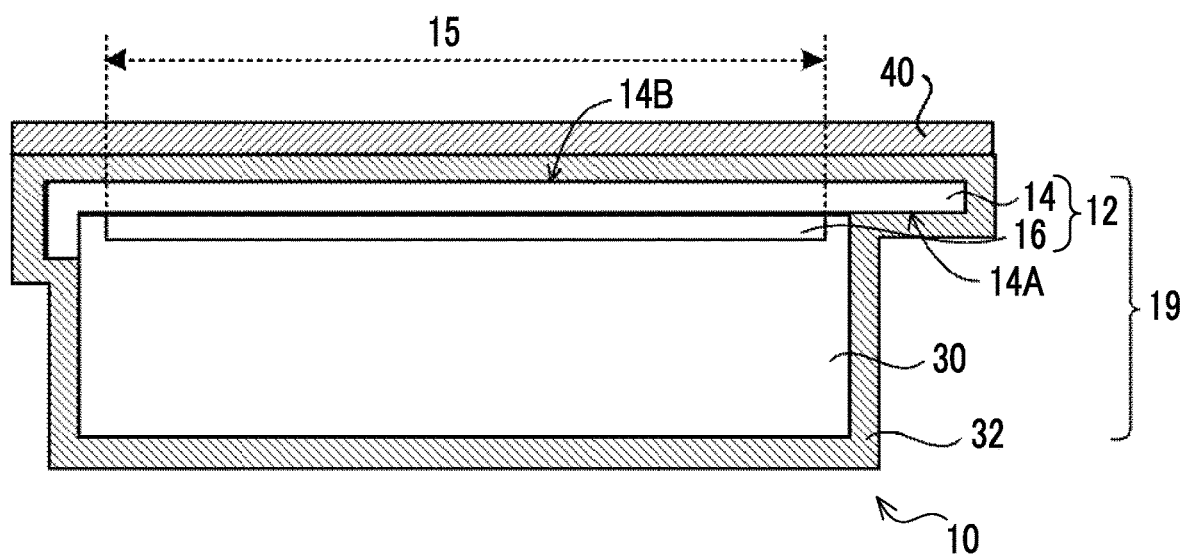
FIG. 10 is a cross-sectional view of another example of the radiation detector of the embodiment.

In addition, in the present embodiment, a form in which the protective film 32 covers the entire laminated body in which the grid 40, the sensor substrate 12, and the conversion layer 30 are laminated. However, the region where the protective film 32 is provided is not limited to the present embodiment. For example, as illustrated in FIG. 10, the protective film 32 may cover the entire laminated body 19 in which the sensor substrate 12 and the conversion layer 30 are laminated. In this case, as illustrated in FIG. 10, the grid 40 is disposed on the second surface 14B side of the base material 14 of the laminated body 19 in a state where being covered with the protective film 32. In the radiation detector 10 illustrated in FIG. 10, the sensor substrate 12 and the grid 40 are not integrated together by the protective film 32. Accordingly, replacement or the like of the grid 40 becomes easy, for example, in a case where replacement with a grid 40 having different intervals of the meshes 45 by the radiation absorbing member 41 of the removal portion 40B is made.

Figure 11:
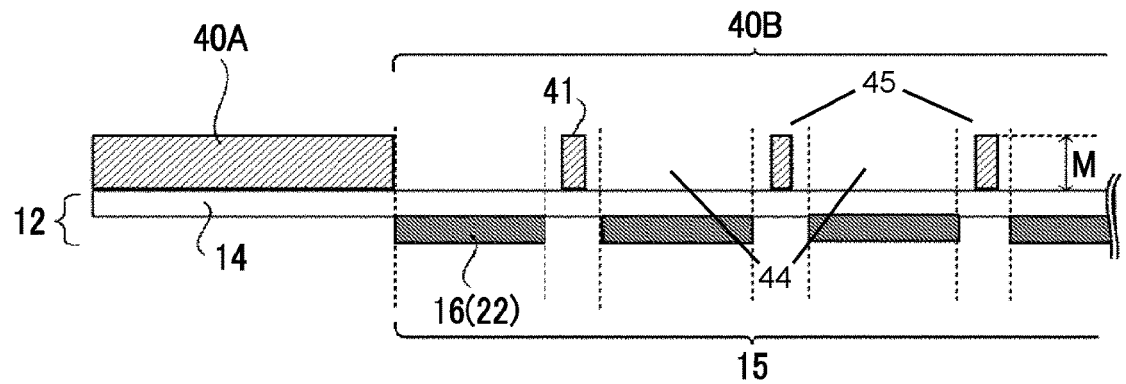
FIG. 11 is a cross-sectional view of still another example of the grid of the present embodiment.

Additionally, in a case where tomography is carried out, the angle of incidence of the radiation that is radiated to the radiation detector 10 varies by about ±20° because imaging is performed multiple times while changing an angle at which radiation is radiated. For that reason, in order to reduce the occurrence of the vignetting resulting from the oblique incidence of the radiation, as illustrated in FIG. 11, the width of the meshes 45 may be smaller in accordance with the distance between the sensor substrate 12 and the tube, or the meshes may be formed so as to become a parallel grid. Additionally, since the incidence angle of the radiation is fixed in the case of a device that does not carry out tomography, the meshes may be formed so as to become a convergence grid. In order to form the convergence grid, the convergence grid may be formed by further forming an absorption layer top after the meshes are formed as one layer by etching and by repeating the etching multiple times so as to have an angle of the convergence grid. The meshes may be formed by overlapping a plurality of films on each other, the meshes being in each of the films formed so as to form the convergence grid. Additionally, grids to be bonded may be selected in accordance with the specifications of these devices.

In addition, in any form, it is preferable that the protective film 32 is provided in a state where the base material 14 is bent. Additionally, in the present embodiment, the form in which the protective film 32 is the single film has been described. However, the protective film 32 may include a plurality of protective films.

Figure 12:
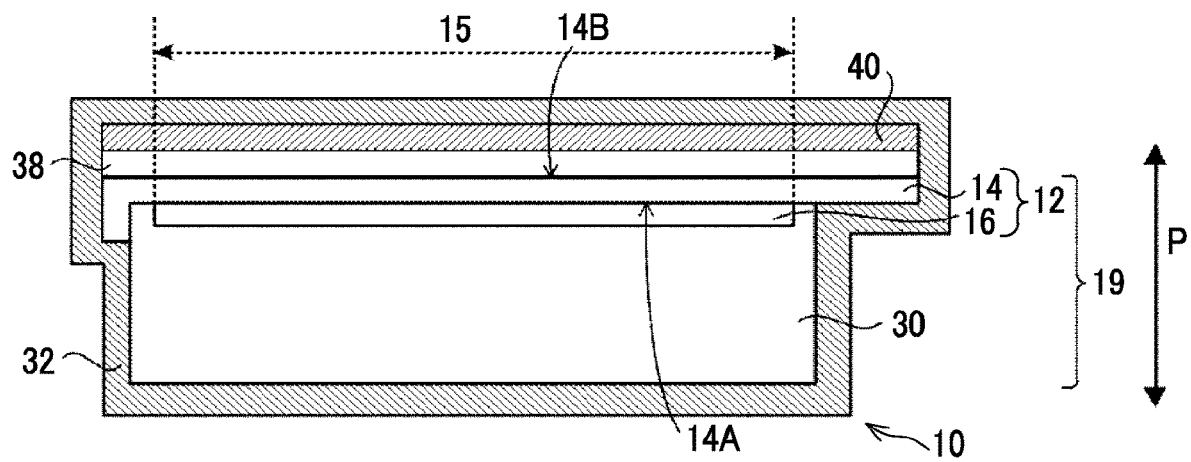
FIG. 12 is a cross-sectional view of still another example of the radiation detector of the embodiment.

Additionally, in the radiation detector 10, layers or films having other functions may be provided on the conversion layer 30 side of the laminated body 19 or on the sensor substrate 12 side. For example, as in an example illustrated in FIG. 12, an antistatic film 38 may be provided on the second surface 14B side of the base material 14. As the antistatic film 38, for example, an ALPET (registered trademark) sheet obtained by laminating aluminum, such as bonding aluminum foil, on the insulating sheet (film), such as polyethylene terephthalate, a film using an antistatic coating material "COLCOAT" (trade name: made by COLCOAT CO., LTD), PET, polypropylene, and the like are applicable.

Figure 13:
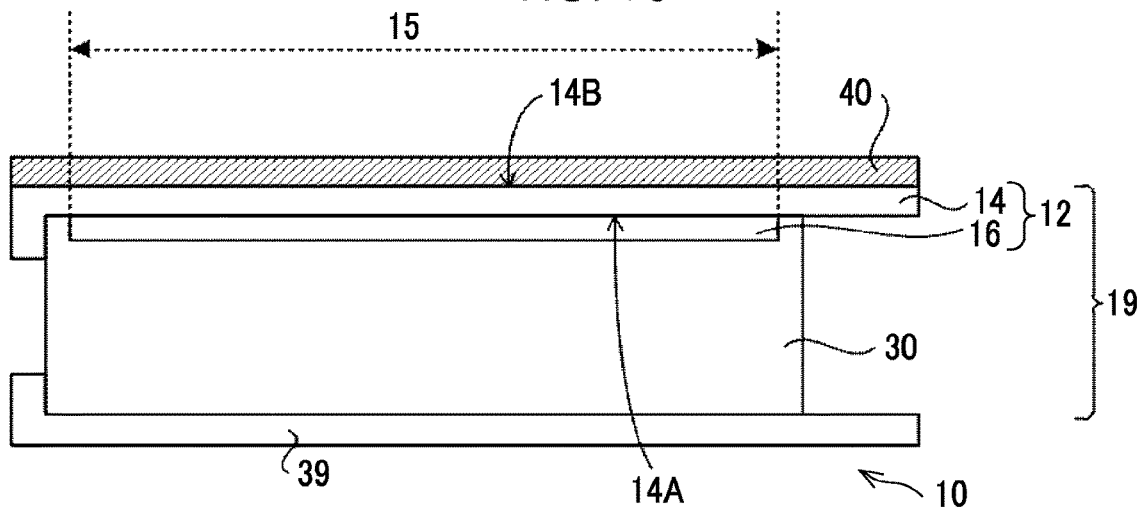
FIG. 13 is a cross-sectional view of a still further example of the radiation detector of the embodiment.

Additionally, for example, as in an example illustrated in FIG. 13, an elastic layer 39 may be provided on the side of the conversion layer 30 opposite to the side where the sensor substrate 12 is provided. The elastic layer 39 has a restoring force that returns the sensor substrate 12 to a state before deflection in a case where the deflection has occurred in the sensor substrate 12 (base material 14). Specifically, the elastic layer 39 has a higher restoring force against the deflection than the sensor substrate 12, and has a higher stiffness than the sensor substrate 12 in order to make the sensor substrate 12 (base material 14) less susceptible to the deflection. As the elastic layer 39 having such characteristics, it is preferable to use an organic material, and a sheet or the like in which at least one of, for example, PET, white PET, foamed white PET, or the like is used as a material is preferable.

Additionally, in the present embodiment, a form in which only the one side of the rectangular base material 14 is bent has been described. However, the invention is not limited thereto, and a plurality of sides may be bent similarly.

Moreover, the configurations, manufacturing methods, and the like of the radiographic imaging apparatuses 1, the radiation detectors 10, and the like that are described in the respective above embodiments are merely examples, and can be modified in accordance with situations without departing from the scope of the invention.

Additionally, in each of the above embodiments, as illustrated in FIG. 1, an aspect in which the pixels 16 are two-dimensionally arranged in a matrix has been described. However, the invention is not limited to this, and the pixels 16 may be one-dimensionally arranged or may be arranged in a honeycomb arrangement. Additionally, the shape of the pixels is also not limited, and may be a rectangular shape, or may be a polygonal shape, such as a hexagonal shape. Moreover, that the shape of the active area 15 is also not limited.

What is claimed is:

1. A radiographic imaging apparatus comprising:
a sensor substrate including a flexible base material, and a pixel region provided on a first surface of the base material, the pixel region including a plurality of pixels that accumulate electrical charges generated in accordance with light converted from radiation;
a conversion layer provided on the first surface side of the sensor substrate to convert radiation into the light;
a grid disposed on a second surface side of the base material opposite to the first surface of the base material and having a removal portion that removes scattered radiation, the removal portion including a radiation absorbing member formed in a mesh such that openings of the mesh partition a predetermined number of pixels into units and respective warp and weft lines of the mesh are provided between the respective units; and
an elastic layer provided on a side of the conversion layer opposite to a side where the sensor substrate is provided.

2. The radiographic imaging apparatus according to claim 1,
wherein the removal portion is disposed in a region corresponding to the pixel region of the sensor substrate, and
wherein the grid further includes an absorption portion provided on the second surface of the base material and including a planar radiation absorbing member, the planar radiation absorbing member covering a region that corresponds to an outside of the pixel region.

3. The radiographic imaging apparatus according to claim 1, wherein the base material has a polygonal shape in a plan view as seen from the first surface side, and a region, corresponding to the outside of the pixel region, at one side of the polygonal shape is bent toward the conversion layer side.

4. The radiographic imaging apparatus according to claim 3, wherein the polygonal shape is a rectangular shape.

5. The radiographic imaging apparatus according to claim 3, further comprising a housing that houses the sensor substrate, the conversion layer, and the grid,
wherein a distance between the sensor substrate and an inner surface of the housing that faces the sensor substrate is shorter on a side where the base material of the sensor substrate is bent than on a side opposite to the bent side.

6. The radiographic imaging apparatus according to claim 1, further comprising a housing that comprises an imaging surface irradiated with radiation and houses the sensor substrate, the conversion layer, and the grid in a state where the sensor substrate is disposed closer to the imaging surface side than the conversion layer.

7. The radiographic imaging apparatus according to claim 1, wherein a width of the warp and the weft lines of the mesh is the same as an interval between the plurality of pixels.

8. The radiographic imaging apparatus according to claim 1, further comprising a protective film that covers an entire laminated body in which the sensor substrate, the conversion layer, and the grid are laminated.

9. The radiographic imaging apparatus according to claim 1, further comprising a protective film that covers an entire laminated body in which the sensor substrate and the conversion layer are laminated.

10. The radiographic imaging apparatus according to claim 1,
wherein the base material has a first alignment mark for alignment, and
wherein the grid has a second alignment mark corresponding to the first alignment mark.

\* \* \* \* \*